United States Patent
Takaiwa et al.

(10) Patent No.: US 6,576,820 B1
(45) Date of Patent: Jun. 10, 2003

(54) TRANSGENIC PLANT EXPRESSING SOYBEAN GLYCININ

(75) Inventors: Fumio Takaiwa, Tsukuba (JP); Shigeru Utsumi, Uji (JP); Tomoyuki Katsube-Tanaka, Koyama (JP)

(73) Assignees: National Institute of Agrobiological Sciences (JP); Bio-Oriented Technology Research Advancement Institution (JP)

( * ) Notice: Subject to any disclaimer, the term of this patent is extended or adjusted under 35 U.S.C. 154(b) by 0 days.

(21) Appl. No.: 09/762,381

(22) PCT Filed: Mar. 14, 1999

(86) PCT No.: PCT/JP99/01057

§ 371 (c)(1), (2), (4) Date: Aug. 13, 2001

(87) PCT Pub. No.: WO00/08161

PCT Pub. Date: Feb. 17, 2000

(30) Foreign Application Priority Data

Aug. 7, 1998 (JP) ............................................. 10-223897

(51) Int. Cl.[7] ............................. A01H 5/00; A01H 1/00; C07H 21/02; C07H 21/04; C12N 15/82
(52) U.S. Cl. .................... 800/320.2; 800/298; 800/278; 800/287; 536/23.1; 536/23.6; 435/468
(58) Field of Search ................................. 800/287, 298, 800/320.2, 278; 536/23.1, 23.6, 24.1; 435/468; 530/370, 372, 378

(56) References Cited

FOREIGN PATENT DOCUMENTS

JP          2-156889 A      6/1990

OTHER PUBLICATIONS

Sindhu et.al.; The pea seed storage protein legumin was synthesized, processed, and accumulated stably in transgenic rice endodperm, 1997, Plant Science 130:189–196.*

Utsumi et.al.; Expression and accumulation of normal and modified soybean glycinins in potato tubers, 1994, Plant Science 102: 181–188.*

Katsube et al., "Development of Rice Plant Producing Soybean Glycinin: Expression and Accumulation in Rice Seeds," *Ann. Mtg. of Japan Soc. For Bioscience, Biotech., and Agrochem.*, 72:164 (Abstract No. 2D1 p21) (Apr. 1, 1998).

Page from *The Chugoku Shimbun*, Chugoku Shimbum Co., Ltd. (Jun. 9, 1998) (translation).

Page from *The Kyoto Shimbun*; Kyoto Shimbun Co., Ltd. (Jun. 9, 1998) (translation).

Page from *The Sankei Shimbun*, SANKEI Shimbun Co., Ltd. (Jun. 9, 1998) (translation).

Page from *The San–in Chuo Shimpo*, San–in Chuo Shimpo Newspaper Co., Ltd. (Jun. 9, 1998) (translation).

Page from *The Japan Agricultural News*, National Press and Information Federation of Agricultural Co–operatives (Jun. 9, 1998) (translation).

Page from *The Japan Industrial Journal* (Jun. 23, 1998) (translation).

Page from *Shohkei Advice*, Shohkei Advice Co., Ltd. (Jun. 25, 1998) (translation).

* cited by examiner

*Primary Examiner*—Elizabeth F. McElwain
*Assistant Examiner*—Stuart F Baum
(74) *Attorney, Agent, or Firm*—Nixon Peabody LLP (57) ABSTRACT

A region containing the glutelin gene promoter, which expresses a gene specifically in the endosperm of rice plant seed, was isolated; a vector was constructed to have the natural or modified soybean glycinin gene ligated downstream of the promoter; the vector construct was introduced into a cultured cell of rice plant; and thus a transgenic rice plant was obtained. The inventors studied the tissue specificity and form of soybean glycinin expressed in the created transgenic rice plant, and then found that the expressed soybean glycinin was accumulated in rice plant seeds in the transgenic rice plant and that the accumulated soybean glycinin was present as the matured protein formed by protein processing.

6 Claims, 8 Drawing Sheets

TRANSGENIC PLANT EXPRESSING SOYBEAN GLYCININ

This application is a national stage filing of PCT/JP99/01057, filed on Mar. 4, 1999, under 35 U.S.C. §371. This application claims priority under 35 U.S.C. §119 and 365 to application number 10/223897 filed in Japan on Jul. 8, 1998.

TECHNICAL FIELD

The present invention relates to a plant expressing soybean glycinin, which is useful as an ingredient in food, and to a propagation material of the plant, and the invention belongs to the fields of agriculture, food, and the like.

BACKGROUND ART

Soybean-extract protein (which has soybean globulin for its main ingredients), which is obtained by extracting proteins from soybeans and acid-precipitating the proteins (pH 4.5), is useful for preventing and treating arteriosclerosis and coronary heart diseases because it lowers the serum cholesterol level in human; particularly, it has the remarkable effection lowering a total cholesterol level, an LDL-cholesterol level, and a triglyceride level in patients with hypercholesterolemia (Mercer, N. J. H., Carroll, K. K., Giovannetti, P. M., Steinke, F. H. and Wolfe, B. M., Nutr. Rep. Int., 35, 279–287 (1987); T. Imura, M. Tanaka, T. Watanabe, S. Kudo, T. Uchida and T. Kanazawa, Ther. Res., 17, 2451–2456 (1996); M. Kanno, Food Industry, 39(18), 59–68 (1996)). In addition, the protein extract significantly reduces a total cholesterol level in healthy persons whose cholesterol levels are within normal limits (Kito, M., Moriyama, T., Kimura, Y. and Kambara, H., Biosci. Biotech. Biochem., 57, 354–355 (1993); Kambara, H., Nohara T., Kito, M., Ther. Res., 14, 3197–3204 (1993)).

By inhibiting the absorption of cholesterol and bile acid, soybean proteins play a pivotal role in lowering the cholesterol level (M. Kanno, Food Industry, 39 (18), 59–68 (1996)). Namely, the inhibition of cholesterol absorption results in an increase in cholesterol synthesis in the liver. However, the re-absorption of bile acid is inhibited at the same time and, as a result, cholesterol in the liver is oxidized into bile acid. This reduces the hepatic cholesterol concentration: and enhances the uptake of serum cholesterol into the liver. Thus, the serum cholesterol level is lowered (M. Kanno, Food Industry, 39(18), 59–68 (1996)).

It has been known that, an indigestible fraction obtained by intensive digestion of soybean protein with a protease markedly lowers the serum cholesterol level (M. Kanno, Food Industry, 39(18), 59–68 (1996)). The primary structure of the peptide present in the indigestible fraction still remains to be clarified (M. Kanno, Food Industry, 39(18), 59–68 (1996)). On the other hand, it has been reported that a peptide derived from A1aB1b subunit of glycinin, which is a major constituent of soybean globulins, has the bile acid-binding activity (Y. Makino, Food Industry, 39(24), 77–87 (1996)), and thus, the above-mentioned indigestible fraction has been believed to be derived from the bile acid-binding peptide originating from the A1aB1b subunit (M. Kanno, Food Industry, 39(18), 59–68 (1996)). Furthermore, a hydrophobic peptide derived from soybean protein is known to have bile acid-binding activity (Iwami, K., Sakakibara, K. and Ibuki, F., Agric. Biol. Chem., 50, 1217–1222 (1986)). Glycinin is the most hydrophobic protein among soybean globulins and there are two hydrophobic regions in the bile acid-binding peptide of A1aB1b subunit (S. Utsumi, Food Industry, 40(10), 68–79 (1997)). Consequently, it can be considered that, among soybean proteins, glycinin chiefly has the activity lowering the serum cholesterol level and, particularly, A1aB1b subunit is highly responsible for the activity.

Examples of industrial application of soybean-extract protein in the field of food include the following commercial products: Soybean Kara-age (fried soybean) and Protein Ganmo (fried tofu, where tofu is soybean curd) from Fuji Oil Co., Ltd.; G-9 and G-9 100 from Kanesa Co.; and Teriyaki Meatball (grilled meatball in teriyaki style), Hamburger, Pork Frankfurt from Nippon Meat Packers, Inc. However, there has been no report on functional food to which glycinin itself is added.

Furthermore, in the field of agriculture, there is no report on an attempt of giving the properties provided by soybean glycinin to other plants.

DISCLOSURE OF THE INVENTION

The present inventors focused on the above-mentioned properties of soybean glycinin and then predicted that the properties of soybean such as an activity of lowering the cholesterol level should be transplantable to plant species other than soybean by expressing soybean glycinin in these plants. The present inventors further focused on not only the above-mentioned activity of lowering the cholesterol level but also the facts that soybean glycinin protein is water soluble and has a wide variety of uses for processing food like tofu and that it excels nutritionally because it contains an essential amino acid "lysine" abundantly, which is less abundant in rice. Thus, the inventors considered that it could be possible to produce new-type processed foods and new agricultural products having higher nutritive values by expressing soybean glycinin protein in other agricultural plants. Thus, an objective of the present invention is to provide a plant expressing soybean glycinin, particularly agricultural products useful as food.

Figure 1:
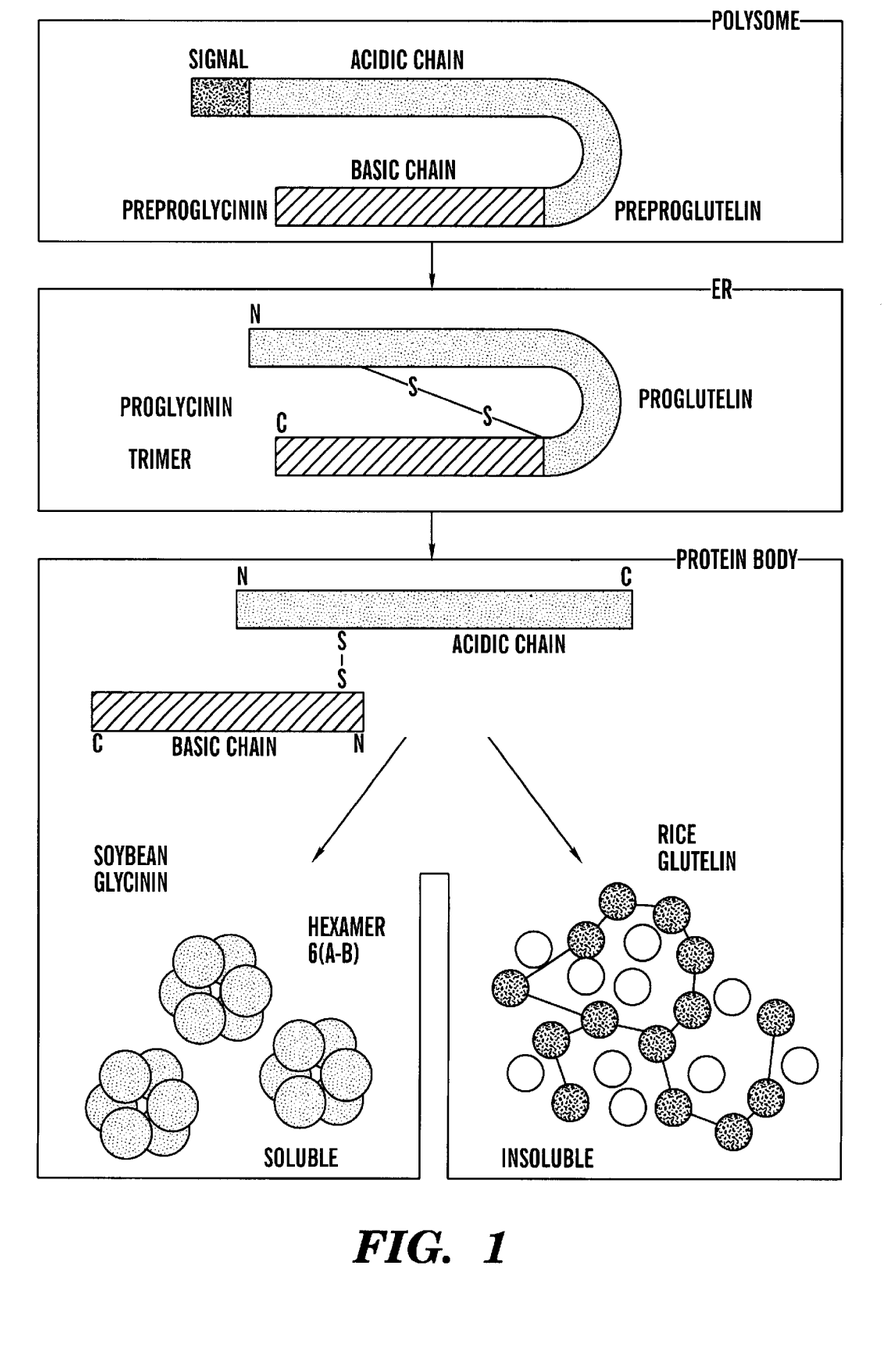
FIG. 1 shows maturation processes of soybean glycinin and rice plant glutelin.

The rice plant, of which seed, rice, is indispensable to Japanese eating habits, is one of the most important agricultural products. A major storage protein, glutelin, accounts for 80% of total protein in rice. Glutelin exhibits 32 to 37% homology to soybean glycinin at the amino acid sequence level, and the two proteins share a fundamental structure. Specifically, both glycinin and glutelin are synthesized as prepro-forms consisting of a signal peptide, A chain, and B chain, converted to pro-forms, and then processed to mature forms by being processed at specific sites of which sequences are highly conserved in each other. There are some differences between them; glycinin forms a trimer and then a hexamer by molecular association and is soluble in a salt solution; glutelin is insoluble in a salt solution because of its own giant molecule formed by disulfide bonding and hydrophobic interaction. Nonetheless, based on the similarity of their fundamental structures, the two proteins are considered to have evolved from the common ancestral gene (FIG. 1). Thus, just as with glutelin, it may be possible, by using glutelin gene promoter, to express and accumulate soybean glycinin, which is excellent in nutrition and processing suitability and has the effect on maintaining and promoting health by lowering the serum cholesterol level in human, in rice seeds, and then new values are thought to be added to rice while the wild-type characteristics of rice are maintained. Furthermore, the accumulation of a hybrid protein of glycinin and glutelin is also promising. Hence,the present inventors selected especially the rice plant as a plant to be used for the expression of soybean glycinin and attempted to express and accumulate soybean glycinin in rice, which is seed of rice plant and is one of useful agricultural products.

Specifically, a region containing the glutelin gene promoter, which expresses a gene specifically in the endosperm of rice plant seed, was isolated; a vector was constructed to have the natural or modified soybean glycinin gene ligated downstream of the promoter; the chimera gene construct was introduced into a cultured cell of rice plant; and thus, a transgenic rice plant was obtained. Subsequently, the inventors studied the tissue specificity and form of soybean glycinin expressed in the created transgenic rice plant. Then, they found that the expressed soybean glycinin was accumulated in rice plant seeds in the transgenic rice plant and the accumulated soybean glycinin was present as a matured protein formed by protein processing. Namely, the present inventors succeeded in expressing and accumulating soybean glycinin as a functional form in rice plant seeds and thus completed the present invention.

The present invention relates to a plant cell and a plant into which the soybean glycinin gene is introduced, preferably relates to a rice plant, and its propagation material, and more specifically relates to:

(1) a transformed plant cell expressively carrying a gene encoding a soybean glycinin protein;

(2) the transformed plant cell of (1), wherein the soybean glycinin protein is A1aB1b subunit;

(3) the transformed plant cell of (1) or (2), wherein the gene encoding a soybean glycinin protein is connected downstream of rice glutelin gene promoter;

(4) a transgenic plant comprising the transformed plant cell of any one of (1) to (3);

(5) the transgenic plant of (4), wherein the transgenic plant is a Poaceae plant;

(6) the transgenic plant of (4), wherein the transgenic plant is a rice plant;

(7) the transgenic plant of any one of (4) to (6), at least in a part of which soybean glycinin protein is accumulated;

(8) a propagation material of the plant of any one of (4) to (6);

(9) the propagation material of (8), wherein the propagation material is a rice seed; and (10) the propagation material of (8) or (9), in which soybean glycinin protein is accumulated.

The present invention relates to a plant cell and a plant into which a gene encoding soybean glycinin protein is introduced and relates to its propagation material.

Soybean glycinin are composed of six subunits, in which A1aB1b, A1bB2, A2B1a, A3B4, and A5A4B3 subunits are assembled nearly at random. (For the structures and sequences of the subunits of glycinin, refer to: Utsumi, S. et al., Marcel Dekker, 257–291, 1997; Utsumi, S. et al., J. Agric. Food.Chem., 35, 210–214, 1987; Cho, T.-J. and Nielsen, N. C., Nucl. Acids Res., 17, 4338, 1989; Utsumi, S. et al., Agric. Biol. Chem., 51, 3267–3273, 1987; Fukazawa, C. et al., J. Biol. Chem., 260, 6234–6239, 1985; Momma, T. et al., Eur. J. Biochem., 149, 491–496, 1985.) In the present invention, there is no particular limitation on the genes encoding soybean glycinin protein to be expressed in a plant cell, as far as the genes encode the soybean glycinin subunits. However, particularly preferred is the gene encoding A1aB1b subunit (SEQ ID NO: 1), which has been known to show the effect on lowering the cholesterol level, etc., or the gene encoding A1bB2 or A2B1a subunit, which is thought to exhibit a similar effect. In the present invention, these subunits may be expressed singly or in combination in a plant cell.

Furthermore, a functional derivative of soybean glycinin protein may also be expressed instead of the natural one. The "functional derivative" means a protein of which amino acid sequence has one or more amino acid substitutions, deletions, and/or additions as compared with that of the natural protein and which is functionally equivalent to the natural protein. The term "functionally equivalent" means that the mutated protein has the activity of lowering the cholesterol level, characteristics for food processing, and/or nutritive properties equivalent to those of the natural protein. While the functional derivatives can be naturally occurring, they can also be prepared artificially. The artificial preparation method includes, for example, a method of substituting a particular amino acid(s) (one or more residues) with other amino acids, deleting a particular amino acid(s) (one or more residues), or inserting an amino acid(s) (one or more residues) at a particular site in a site-specific manner by using a single-stranded oligonucleotide, as well as a method of altering amino acid sequence by inserting, substituting, or deleting a double-stranded foreign gene or a synthetic gene using a particular restriction site (refer to Utsumi, S., Adv. Food Nutr. Res., 36, 89–208, 1992).

There is no particular limitation on the plant cell into which the soybean glycinin gene is to be introduced, and it is possible to use a cell from any plant species. However, particularly preferred is a cell of agricultural crops because the purpose of the present invention is to exert the function of soybean glycinin such as the function lowering the cholesterol level in the living body. The agricultural crops include, for example, grain crops such as rice plant, barley, wheat, rye, and maize; leguminous crops such as haricot, faba bean, and garden pea; oilseed crops such as peanut, sesame, colza, cotton, sunflower, and safflower; crops forming tuberous root such as potato and sweet potato; crops having fruit such as apple, melon, and grape; and crops of which leaf is used for food such as spinach, qing-geng-cai, and cabbage. In the present invention, the plant cell into which the soybean glycinin gene is to be introduced includes every type of plant cell capable of growing to be a plant. For example, this includes a cultured cell, protoplast, shoot primodium, multiple shoot, hairy root, and callus, but is not limited to these examples. The plant cell in the invention includes a cell in a plant.

In order to express the soybean glycinin gene in a plant cell, a DNA molecule comprising the following elements is introduced into the plant cell: (i) a promoter sequence having the activity of transcription activation in the plant cell, (ii) the soybean glycinin gene ligated downstream of the promoter sequence in sense-orientation, and (iii) terminator sequence, which contains a sequence segment required for transcription termination and polyadenylation, ligated downstream of the gene. Such a DNA molecule may contain a DNA sequence element that is capable of enhancing the transcription, other than the promoter element, for example, an enhancer sequence.

There is no particular limitation on the promoter to be used, as far as the promoter is functional in the plant cell. However, preferred is a tissue-specific promoter that secures the effective expression of the glycinin gene at a desired site in a regenerated plant. Preferable tissue-specific promoters include, for example, glutelin gene promoter for the expression in rice plant seed (Takaiwa, F. et al., Plant Mol. Biol., 17, 875–885, 1991); glycinin gene promoter or a promoter of the major storage protein gene in each crop for the expression in the seeds of leguminous crops such as haricot, faba bean, and garden pea or oilseed such as peanut, sesame seed, colza, cotton seed, sunflower, and safflower; for example, phaseolin gene promoter for the expression in haricot (Murai, N. et al., Science, 222, 476–482, 1983), and cruciferin gene promoter for the expression in colza (Rodin, J. et al., Plant Mol. Biol., 20, 559–563, 1992); furthermore, patatin gene promoter for the expression in the tuber of potato (Rocha-Sosa, M. et al., EMBO J., 8, 23–29, 1989), and sporamin gene promoter for the expression in the tuberous root of sweet potato (Hattori, T. and Nakamura, K., Plant Mol. Biol., 11, 417–426, 1988); ribulose-1,5-bisphosphate decarboxylase gene promoter in a leaf of vegetable such as spinach (Orozco, B. M. and Ogren, W. L., Plant Mol. Biol., 23, 1129–1138, 1993). These specific examples of promoter are just illustrative, and a variety of promoters other than these are usable for each practical purpose. In addition, it is possible to use not only the above-mentioned tissue-specific promoters but also constitutive promoters such as 35S promoter as well as inducible promoters.

Introduction of the soybean glycinin gene into a plant cell can be achieved by various methods that are known to those skilled in the art. For example, the following method can be used: an indirect introduction method using *Agrobacterium tumefaciens* or *Agrobacterium rhizogenes* (Hiei, Y. et al., Plant J., 6, 271–282, 1994; Takaiwa, F. et al., Plant Sci. 111, 39–49, 1995) or a direct introduction method represented by electroporation method (Tada, Y. et al. Theor. Appl. Genet, 80, 475, 1990), polyethylene glycol method (Datta, S. K. et al., Plant Mol Biol., 20, 619–629, 1992), or particle gun method (Christou, P. et al., Plant J. 2, 275–281, 1992; Fromm, M. E., Bio/Technology, 8, 833–839, 1990).

Regeneration of the transformed plant cell enables creating a plant. The method of the regeneration depends on the types of plant cells; representative methods are, for example, the method of Fujimura et al. for rice plant (Fujimura, T. et al., Plant Tissue Culture Lett., 2, 74, 1995); the method of Armstrong et al. for maize (Armstrong, C. L. and Phillips, R. L., Crop Sci., 28, 363–369, 1988); the method of Radke et al. for colza (Radke S. E., Theor. Appl. Genet. 75, 685–694, 1988); and the method of Sheerman et al. for potato (Sheerman, S. and Bevan, M. W., Plant Cell Rep., 7, 13–16, 1988).

Because of the expression of introduced soybean glycinin gene, soybean glycinin protein is expressed and accumulated in target regions of a plant originating from the created transgenic plant or its propagation material, for example, seed, tuberous root, tuber, fruit, cutting, etc. Thus, the characteristics of soybean glycinin protein, such as nutritive properties, characteristics for food processing, and promoting activity for health, can be imparted to other plant species.

BEST MODE FOR CARRYING OUT THE INVENTION

The present invention is illustrated in detail below with reference to Examples, but is not to be construed as being limited thereto.

Example 1

Construction of a Soybean Glycinin Expression Vector and Creation of a Transformed Rice Plant Expressing Soybean Glycinin (1) Isolation of Soybean Glycinin cDNA An expression plasmid for soybean glycinin was constructed, which was to be used for the transformation of rice. Specifically, an XhoI fragment (1.7 kb) from pUG1 containing A1aB1b cDNA (S. Utsumi, S. Kitagawa, T. Katsube, I. J. Kang, A. B. Gidamis, F. Takaiwa, and M. Kito, 1993, 92(2): 191–202) was repaired by using Klenow enzyme in the presence of dNTP.

(2) Insertion of Soybean Glycinin cDNA Into a Vector Encompassing Rice Plant Glutelin Gene Promoter The DNA of genomic clone λINE9 of the glutelin GluB-1 gene (Takaiwa, F. et al., Plant. Mol. Biol. 17, 875–885, 1991) was first digested with restriction enzymes, KpnI and EcoRI. A subclone Kpn9 was obtained by cloning a fragment containing both glutelin gene promoter and the N-terminal coding region. Then, the subcloned DNA was digested with a restriction enzyme, Sau3A, to give a 1.6-kb Sau3A fragment which contains the transcribed region (330 bp) of the rice plant glutelin gene and its 5'-upstream region (1.3 kb). The coding region for glutelin was removed by digesting the plasmid at a restriction enzyme site of AflII, which was present at nucleotide position +18 relative to the transcription initiation site of the glutelin gene, and at a SmaI site in pUC118 vector; and, instead of the removed fragment, the glycinin cDNA prepared in (1) was inserted into the corresponding site. The orientation of the insert was verified by using an EcoRI site in the glycinin cDNA and a HindIII site in pUC118 vector.

Figure 2:
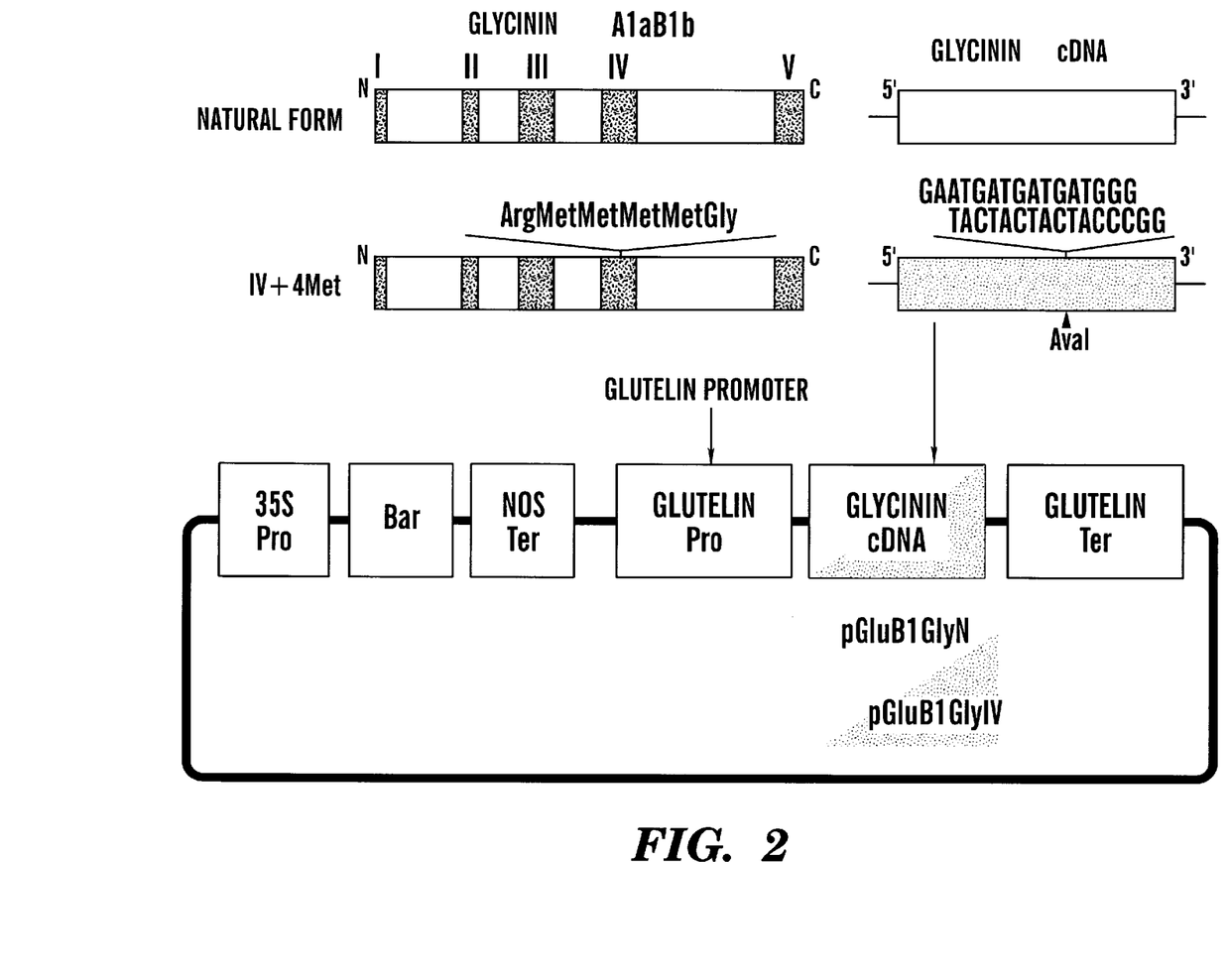
FIG. 2 illustrates plasmids, "pGluB1GlyN" and "pGluB1GlyIV," which were used for the transformation of rice plant in the present invention.

A fragment containing the GluB-1 promoter (from −1302 to +18) and the glycinin cDNA was digested with HindIII and SacI, and then recovered; the fragment was inserted into pUC18 containing the 3'-untranslated region (0.7 kb) of GluB-1, CaMV 35S promoter, bialaphos-resistance gene (BAR), and a terminator of the nopalin synthetic gene (NOS terminator). The plasmid constructed was named "pGluB1Gly." Similarly, a plasmid of a chimera gene containing a modified glycinin cDNA (pUG1IV) (S. Utsumi, S. Kitagawa, T. Katsube, I. J. Kang, A. B. Gidamis, F. Takaiwa, and M. Kito, 1993, Plant Sci., 92(2): 191–202) and GluB-1 promoter (from −1302 to +18) was also constructed. The plasmid obtained was designated as "pGluB1GlyIV." The plasmids constructed are schematically shown in FIG. 2.

The transformant was prepared by the following method. A rice plant callus was induced from a scutellum of fully ripened seed, and the callus was cultivated in a modified N6 medium. After the protoplast was isolated according to the method of Fujimura et al. (Fujimura, T., et al., Plant Tissue Culture Lett. 2, 74–75, 1985), then protoplast cultivation was performed according to the method of Ohtsuki et al. (Y. Ohtsuki et al., "Conditions of suspension culture associated with efficient preparation of rice plant protoplast" Ikushugaku-zasshi (Journal of Breeding), vol.35, suppl.1, 78–79).

A plasmid containing the chimera gene was directly introduced into the protoplast by electroporation. Electroporation was performed by using ASP buffer of Tada et al. (Tada, Y. et al., Theor. Appl. Genet, 80, 475–480, 1990) with the plasmid (20 μg/ml) under conditions of 750 V/cm and 40 msec. In the selection of recombinants, bialaphos was added as a selection marker to the protoplast medium, callus growth medium, and re-differentiation medium at a concentration of 10 mg/l.

The plasmids, "pGluB1Gly" and "pGluB1GlyIV," were introduced into 68 individuals and 52 individuals, respectively, of a rice strain, Matsuyama Mitsui; and also into 26 individuals and 15 individuals, respectively, of another rice strain, Himenomai. The individuals were completely grown to be mature. Regeneration of a plant was carried out according to the method of Ozawa et al. (Ozawa, K. and Komamine, A., Theor. Appl. Genet, 77, 205–211, 1989). Insertion of the glycinin gene and the BAR gene in the rice plant genome was verified by PCR using primers specific to the glutelin promoter and the soybean glycinin gene.

Example 2

Preparation of Recombinant Proteins of Glutelin and Glycinin

Each portion of cDNA corresponding to mature protein of glutelin (GluA-1, GluB-1) or glycinin (A1aB1b) was obtained by PCR. Primer pairs used for the PCR amplification were as follows: GluA-1 (SEQ ID NO: 2/5'-CAGCAGCTATTAGGCCAGAGCACTAG-3', SEQ ID NO: 3/5'-GGGAAGCTTTATCCGCAAGCCGACCTAAG-3'); GluB-1 (SEQ ID NO: 4/5'-CAGCTATTTAATCCCA-GCACAAACCC-3', SEQ ID NO: 5/5'-GGGAAG-CTTACATTACTCTGAGGTCTCGC-3'); and A1aB1b (SEQ ID NO: 6/5'-TTCAGTTCCAGAGAGCAGCC-3', SEQ ID NO: 7/5'-CGCGGATCCATACAAAAAGGG-CTCTAAG-3'). The latter primer in each primer pair corresponds to the complementary strand of nucleotide sequence encoding C-terminal portion of each mature subunit. The latter primer for GluA-1 or GluB-1 has a HindIII site, and the latter primer for A1aB1b has a BamHI site. The fragment amplified by PCR was blunted at its ends by using a blunting kit (Takara Shuzo Co.) and then digested with HindIII (for GluA-1 and GluB-1) or BamHI (for A1aB1b). The resulting DNA fragment was inserted into pET-21d vector (Novagen Co.) between the NcoI site which had been filled in by repair) and the HindIII site (for GluA-1 and GluB-1) or between the NcoI site (which had been filled in by repair) and the BamHI site (for A1aB1b), thereby constructing E. coli expression plasmids, pEGluA-1, pEGluB-1, and pEA1aB1b. Cells of E. coli BL21 (DE3) bearing each expression plasmid were grown in LB medium, until the absorbance at 600 nm reached 0.6. Then IPTG (final concentration; 1 mM) was added to the culture at 37° C. to induce the expression.

Example 3

Preparation of Anti-glutelin GluA-1 Antiserum and Anti-glutelin GluB-1 Antiserum E. coli cells expressing pro-glutelin GluA-1 or GluB-1 were sonicated in 35 mM sodium phosphate buffer (pH8.0),
0.1 M NaCl, 1 mM EDTA, and 1.5 mM phenylmethylsulfonylfluoride (PMSF). E. coli proteins soluble in a salt solution were removed, and then pro-glutelin GluA-1 or GluB-1 was extracted by using 1% (v/v) lactic acid and 1 mM EDTA. The extracted pro-glutelin was dialyzed against 50 mM Tris-HCl buffer (pH8.0), 1 mM EDTA, 1 mM PMSF, 6 M urea, and 0.1 M 2-mercaptoethanol (2ME) (buffer A). The protein sample was subjected to column chromatography using buffer A-pre-equilibrated SP Sepharose FF (2.6× 10 cm) (Pharmacia Co.). Pro-glutelin was eluted with a linear concentration gradient of 0–0.2 M NaCl. The resulting partially purified sample was further purified by SDS-PAGE. Each of GluA-1 and GluB-1 was electroeluted from the single band in the gel. The protein sample was sufficiently dialyzed against 10 mM potassium phosphate buffer (pH7.6) and 6 M urea. Each of the purified pro-glutelins GluA-1 and GluB-1 was emulsified together with Freund's complete adjuvant, and the protein emulsion was injected intracutaneously into a male rabbit (body weight; about 2 kg) according to the method described in a reference (S. Utsumi, S. Kitagawa, T. Katsube, I. J. Kang, A. B. Gidamis, F. Takaiwa, and M. Kito, 1993, Plant Sci., 92(2): 191–202). Immunization schedule was as follows: secondary immunization was conducted two weeks after the primary immunization; the tertiary immunization was carried out three-weeks after the secondary immunization; the quaternary immunization was carried out two weeks after the tertiary immunization; and the antiserum was obtained by blood collection ten days after the quaternary immunization.

Example 4

RNA Blotting

Figure 3:
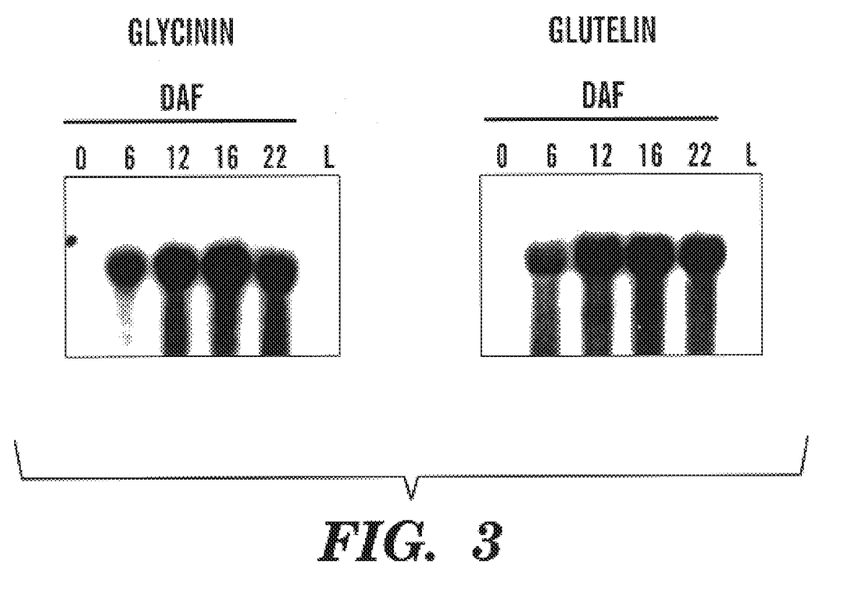
FIG. 3 shows photographs of electrophoretic patterns of Northern blot showing the expression of the glycinin and glutelin genes in fully ripened seeds and leaves in the transgenic rice plant. "DAF" in the figure denotes the number of days after flowering.

RNA was extracted from leaves and ripening seeds of the transgenic plant created in Example 1 according to the method described in a reference (Takaiwa, F. et al., Mol. Gen. Genet., 208, 15–22, 1987). A 15-μg aliquot of total RNA was electrophoresed in a denaturation gel of 1.2% agarose containing formaldehyde and then transferred onto a charged nylon membrane (Amersham Co.). RNA on the membrane was hybridized to a probe of glycinin cDNA in pUG1; the probe was labeled with $^{32}$P by random priming method (Feinberg, A. P. and Vogelstein, B., Anl. Biochem., 13, 6–13, 1983) prior to the use. The expression of the glutelin (GluB-1) gene was also tested for comparison (FIG. 3). The results showed that the glycinin gene was expressed in the process of ripening at a similar level to that of the glutelin gene and that the glycinin gene expression was not detectable in the leaves. Each numeral (0, 5, 12, 16, or 22) in the figure denotes the number of days after flowering.

Example 5

Extraction and Immunological Detection of Proteins

Segregation analysis was carried out by the following procedure. Each of 50 grains of fully ripened seed from an originally transformed plant expressing natural or modified glycinin was independently ground up in a mortar. Proteins were extracted from the powder at 4° C. with 35 mM potassium phosphate buffer (pH7.6), 0.4 M NaCl, 1.5 mM PMSF, and 1 mM EDTA (extraction buffer). An aliquot of the extract (10 μg of proteins) from each of the 50 grains was spotted onto a nitrocellulose membrane, and the expression products on the membrane were detected by using anti-glycinin antiserum and goat anti-rabbit IgG antiserum-alkaline phosphatase conjugate (Promega Co.) (S. Utsumi, T. Sato, C.-S. Kim and M. Kito, 233, 273–276, 1988).

Figure 4:
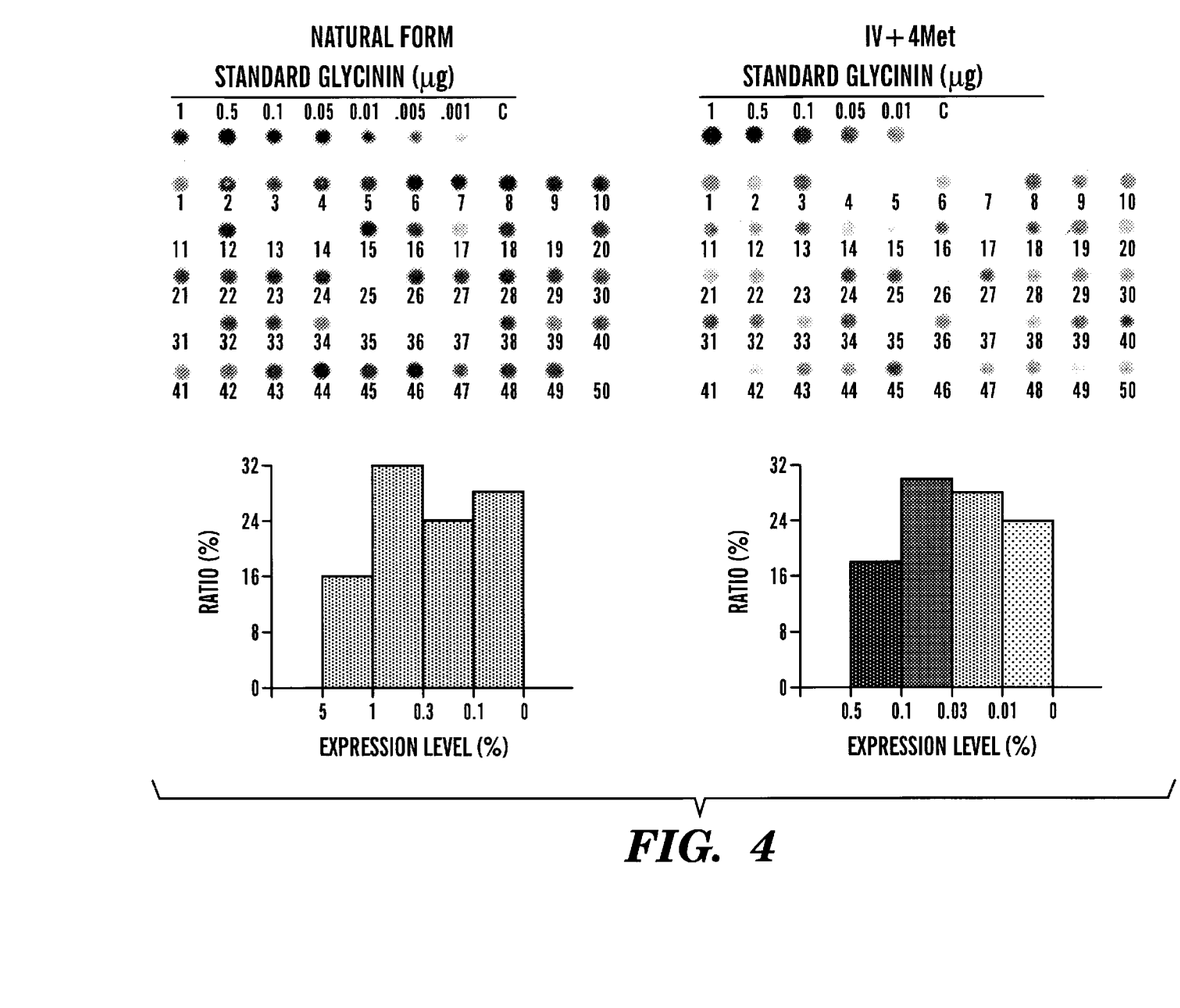
FIG. 4 shows the expression of natural and modified glycinins in fully ripened seeds of the transgenic rice plant. The expression as analyzed by dot blotting.

The results are shown in FIG. 4. The natural protein (in the left panel of the figure) exhibited a maximal expression level of about 5%, while the modified protein, IV+4Met (in the right panel of the figure), showed a maximal expression level of about 0.5%. Frequency distribution of the expression was summarized at the bottom of the figure. The expression levels observed were almost equally distributed in all the four categories, high level, medium level, low level, and almost null level. These results suggest that a single copy or multiple copies of the glycinin gene have been integrated in closely linked genomic regions.

According to the experimental results, there is a difference of an order of magnitude in the maximal expression level between the normal form and IV+4Met. Such a difference is not found in previous experiments where the genes were expressed in tobacco or potato. Furthermore, Northern analysis showed a similar difference in the transcription level. Based on these findings, the difference in the expression level is considered to result from the position effect.

Namely, the seeds exhibiting the high level expression (natural form: 8, 6, 15; IV+4Met: 8, 19, 3) are presumed to be homozygotes of the glycinin gene. Then, using the half-grain analysis, the inventors grew second generations originating from the seeds exhibiting the high level expression. Second-generation seeds resulting from self-fertilization (ten grains each) were tested, and the analytical results showed that all the seeds expressed the gene at high levels. Namely, the present inventors succeeded in integrating the glycinin gene in the genome.

Example 6

Analysis for Self-aggregation Property of Proteins by Sucrose Density Gradient Centrifugation In order to examine the presence of proper processing for the molecular aggregation and protein maturation, seeds from the strains exhibiting the high level expression were subjected to salt-extraction, and the extracts were analyzed by sucrose density gradient centrifugation. Protein extracted from 100 mg of fully ripened seeds by using an extraction buffer was subjected to sucrose density gradient centrifugation according to the method as described in a reference (S. Utsumi, S. Kitagawa, T. Katsube, I. J. Kang, A. B. Gidamis, F. Takaiwa, and M. Kito, 1993, Plant Sci., 92(2): 191–202). The fractions, 2S, 7S, and 11S, purified from soybean seeds by the method of Thanh and Shibasaki (V. H. Thanh and K. Shibasaki, J. Agric. Food Chem., 24, 1117–1121, 1976) were used as size markers in the same analysis. The resulting fractioned samples were subjected to SDS-PAGE and then analyzed by Western blotting. Western blotting was carried out as follows: each sample (25 $\mu$g) was dissolved in 62.5 mM Tris-HCl buffer (pH6.8), 2%(w/v) SDS, and 30% (v/v) glycerol with or without SDS sample buffer (1% (v/v) 2-mercaptoethanol (2-ME)), and then boiled for 3 minutes; the sample was subjected to SDS-PAGE (polyacrylamide concentration; 11% (w/v)). Proteins on the gel were transferred onto a nitrocellulose membrane and analyzed by using anti-pro-glycinin antiserum, anti-glycinin antiserum, and anti-pro-glutelin antiserum in the same manner as described in Example 5.

Figure 5:
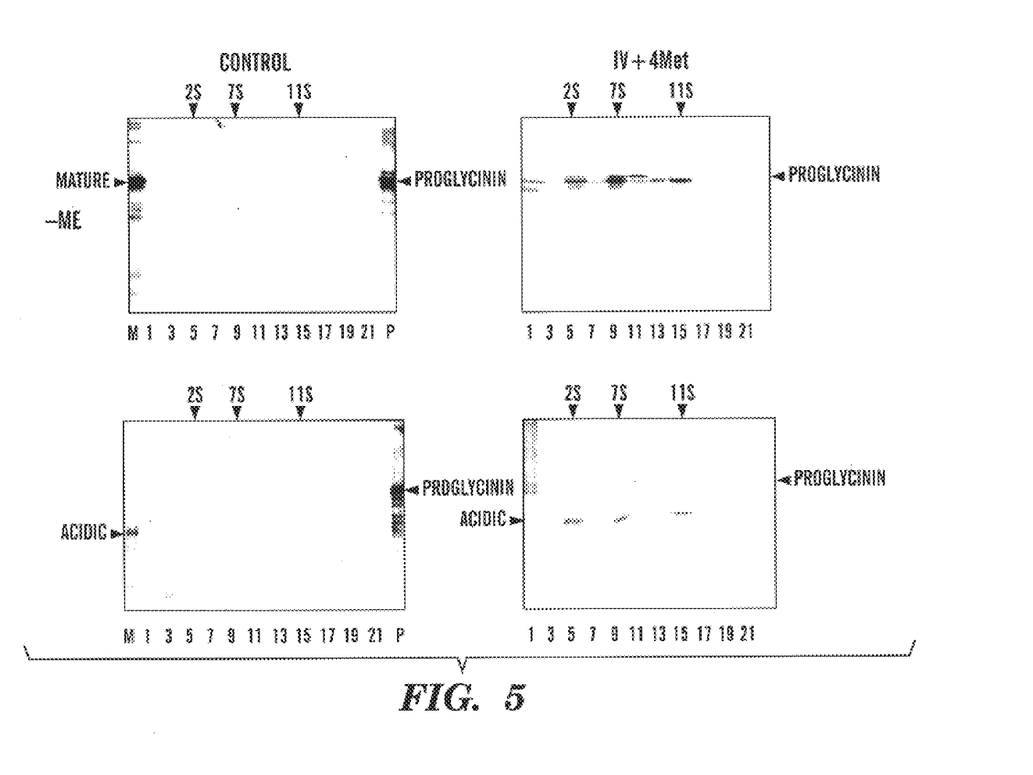
FIG. 5 shows photographs of electrophoretic patterns showing analytical results of the molecular aggregates of natural and modified glycinins expressed in fully ripened seeds of the transgenic rice plant.

The results are shown in FIG. 5. There were bands chiefly in the fractions of 2S, 7S, and 11S corresponding to glycinin monomer, trimer, and hexamer, respectively, in IV+4Met, while such bands were not detected in a non-transformed control. Observed in the absence of the reducing agent were a band corresponding to mature glycinin and a band corresponding to pro-glycinin, which has a slightly larger size than the former. On the other hand, in the presence of the reducing agent, a band corresponding to pro-glycinin was detected only in the fractions 2S and 7S, and a band corresponding to glycinin A-chain was found in all the fractions of 2S, 7S, and 11S. The natural protein also gave the same results as the IV+4Met protein. The experimental results suggest that both natural and modified forms can be matured to be hexamers through molecular association by protein processing.

Figure 6:
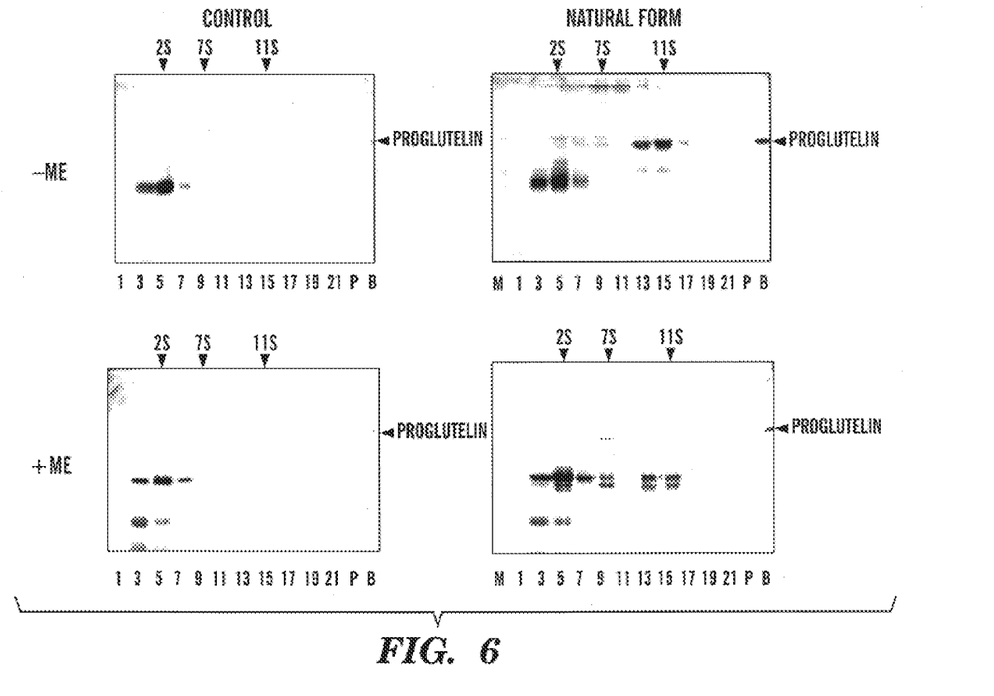
FIG. 6 shows photographs of electrophoretic patterns showing the interaction between soybean glycinin and rice glutelin.

In the next step, interaction between soybean glycinin and rice glutelin both expressed in rice seed was studied. FIG. 6 shows results of similar experiments to those carried out in FIG. 5; a salt extract of rice seed, namely globulin fraction, was separated by sucrose density gradient centrifugation and subjected to SDS-PAGE, followed by Western blotting and detection with the anti-glutelin antibody. A band corresponding to glutelin A-chain was found chiefly in the fraction of 2S in a non-transformed control. On the other hand, in the transformant expressing glycinin, together with the band corresponding to that found in the control, another band was detected chiefly in 11S fraction and also partly in 7S fraction. The band was recognized to correspond to the size of pro-glutelin in the absence of the reducing agent and to correspond to the size of glutelin A-chain in the presence of the reducing agent. In this figure, lane M and lane P contain 1 $\mu$g of mature soybean glycinin and 1 $\mu$g of soybean pro-glycinin, respectively. As clearly seen in this figure, since anti-glutelin antibody was little cross-reactive to these molecular species of soybean glycinin, the band observed in 11S and 7S fractions can be judged to be rice glutelin. In other words, soybean glycinin expressed in rice seed helped a part of glutelin to become soluble in salt solution, namely become globulin. The solubilized protein is present in the fractions of 11S and 7S where glycinin is also present, and accordingly the protein is assumed to form a hetero-hybrid hexamer and hetero-hybrid trimer by interacting with glycinin. The amount of solubilized glutelin was roughly estimated to correspond to about 5% of soluble glycinin.

Example 7

Figure 7:
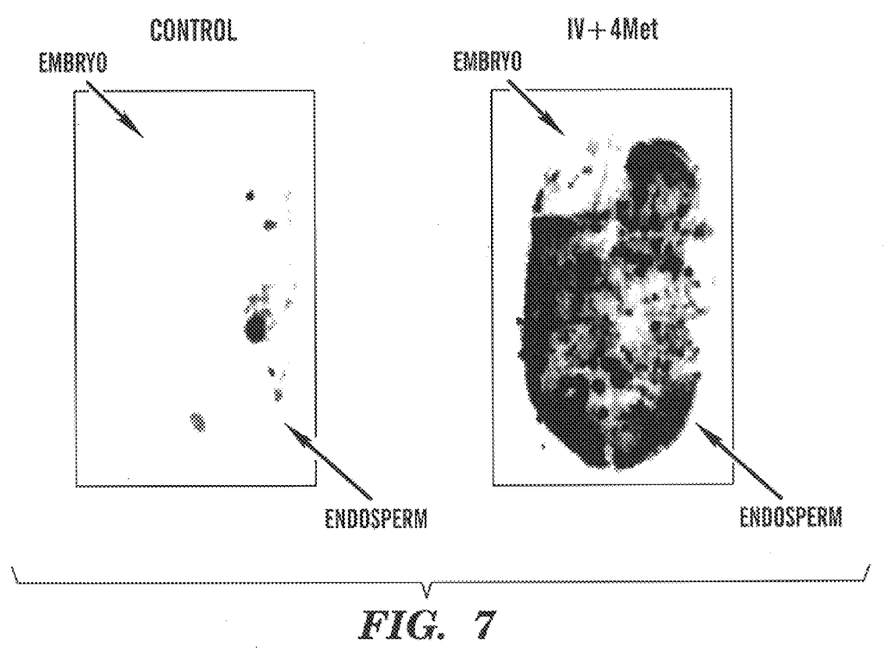
FIG. 7 shows photographs showing in situ expression sites of glycinin in rice seeds. The sites were analyzed by tissue printing.

Analysis for the in situ Expression Site of Glycinin in Rice Seeds by Tissue Printing The glutelin promoter directs the seed endosperm-specific expression. Tissue specificity of the expression was verified by tissue printing. The in situ expression site was analyzed by tissue printing method as described by Manteuffel et al. (R. Mo Manteuffel and R. Ranitz, Plant Mol. Biol., 22, 1129–1134, 1993). A grain of rice seed was immersed in 0.01 M phosphate buffer (pH7.4), 0.8% (w/v) NaCl, 0.2% (w/v) KCl, 10 mM $NaN_3$, and 0.4 M sucrose and then was cut vertically by using a razor blade. Subsequently, the half grain was immersed in acetone for 20 seconds to remove lipids, and then it was pressed down onto a nitrocellulose membrane for 5 to 10 seconds. The nitrocellulose membrane was then dried at 60° C. for 30 minutes and was subjected to immunoblotting using an anti-glycinin antiserum. The results are shown in FIG. 7. The left panel shows a control experiment and the right panel shows the results with IV+4Met. Glycinin was expressed in the endosperm but not in the embryo. The natural form also gave the same results as the modified form IV+4Met. In other words, both the natural form and the modified form were revealed to have the tissue specificity of the expression. In addition, glycinin was detected in matrix portions of protein body, when the endosperm was observed by immunohistochemistry using an electron microscope. Thus, it can be concluded that glycinin expressed is targeted to the protein body.

Example 8

Analysis for the Solubility of Proteins by Serial Extraction

Grains of rice seed (18 mg) were finely ground up and were subjected to extraction with 1800 μl of extraction buffer containing 25 mM N-ethylmaleimide (NEM), where the extraction was repeated continuously six times, each of which was carried out at room temperature for one hour while the mixture was being stirred vigorously. After extraction using the extraction buffer, the resulting residue was further extracted three times with 1800 μl of 1% (v/v) lactic acid, 1 mM EDTA, and 25 mM NEM. In the final step, the residue was yet further extracted once with 1800 μl of SDS sample buffer in the same manner.

Figure 8:
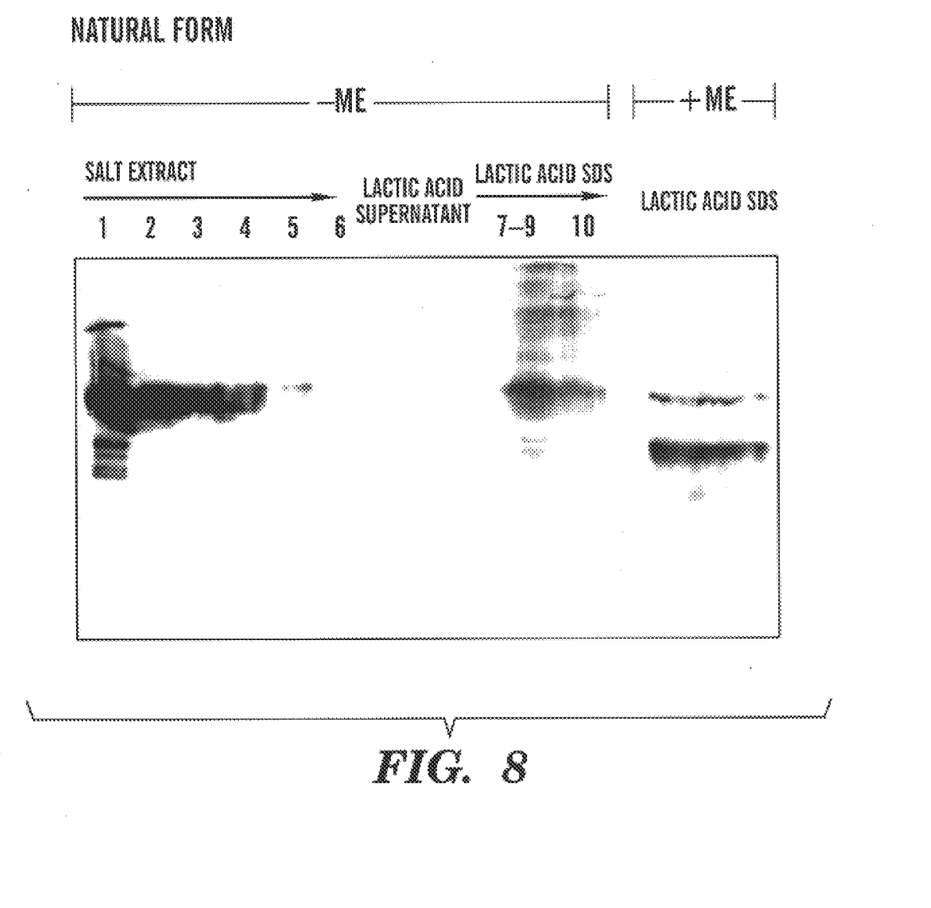
FIG. 8 shows photographs of electrophoretic patterns showing analytical results of the solubility of soybean glycinin by serial extraction treatment.

On the other hand, it was also analyzed whether or not glycinin expressed was assembled with glutelin. Grains of rice seed were sufficiently extracted with a salt solution six times. The grains were further extracted with 1% lactic acid three times, and then once with SDS. The resulting fractions were subjected to SDS-PAGE and then were analyzed by Western blotting using the anti-glycinin antibody. The results are shown in FIG. 8. Glutelin is extracted with lactic acid, but is precipitated when sodium chloride is added to the extract. As clearly seen in the figure, quantity of glycinin extracted by the salt solution decreased as the extraction was repeated, and almost no glycinin was extracted at the sixth round of extraction. Nonetheless, glycinin was extracted again with 1% lactic acid or SDS. This suggests that a part of glycinin expressed interacts and is assembled with rice glutelin. The amount of insoluble glycinin expressed was roughly estimated to be about 20% of total glycinin expressed.

INDUSTRIAL APPLICABILITY

The present invention provides a transgenic plant that expresses soybean glycinin and a propagation material thereof. Soybean glycinin excels in its nutritive properties and characteristics for processing, and has the health-promoting activity that lowers the serum cholesterol level in human. The present invention thus makes it possible to produce agricultural products with new values. Furthermore, soybean glycinin is a protein derived from soybean, which is one of daily foods, and therefore, it is advantageous that the agricultural products produced by the present invention is highly safe.

---

What is claimed is:

1. A transgenic rice plant comprising a rice cell transformed with a gene encoding a soybean glycinin protein.

2. The transgenic rice plant of claim 1, wherein the soybean glycinin protein has an amino acid sequence encoded by SEQ ID NO: 1.

3. The transgenic rice plant of claim 1, wherein the gene encoding a soybean glycinin protein is connected downstream of a rice glutelin gene promoter.

4. The transgenic rice plant of claim 1, wherein the rice plant expresses soybean glycinin protein.

5. A seed of the transgenic rice plant of claim 1, comprising a soybean glycinin gene.

6. The seed of claim 5, in which soybean glycinin protein is expressed.

* * * * *

UNITED STATES PATENT AND TRADEMARK OFFICE
CERTIFICATE OF CORRECTION

PATENT NO. : 6,576,820 B1
DATED : June 10, 2003
INVENTOR(S) : Takaiwa et al.

It is certified that error appears in the above-identified patent and that said Letters Patent is hereby corrected as shown below:

<u>Title page,</u>
Item [22], PCT Filed, "Mar. 14, 1999" should be -- Mar. 4, 1999 --.

Signed and Sealed this

Twenty-fifth Day of November, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 1743
<212> TYPE: DNA
<213> ORGANISM: Glycine max
<220> FEATURE:
<221> NAME/KEY: CDS
<222> LOCATION: (52)..(1536)

<400> SEQUENCE: 1

```
acaactcaaa cattctctcc attggtcctt aaacactcat cagtcatcac c atg gcc      57
                                                          Met Ala
                                                           1 aag cta gtt ttt tcc ctt tgt ttt ctg ctt ttc agt ggc tgc tgc ttc     105
Lys Leu Val Phe Ser Leu Cys Phe Leu Leu Phe Ser Gly Cys Cys Phe
         5                  10                  15 gct ttc agt tcc aga gag cag cct cag caa aac gag tgc cag atc caa     153
Ala Phe Ser Ser Arg Glu Gln Pro Gln Gln Asn Glu Cys Gln Ile Gln
     20                  25                  30 aaa ctc aat gcc ctc aaa ccg gat aac cgt ata gag tca gaa gga ggg     201
Lys Leu Asn Ala Leu Lys Pro Asp Asn Arg Ile Glu Ser Glu Gly Gly
 35                  40                  45                  50 ctc att gag aca tgg aac cct aac aac aag cca ttc cag tgt gcc ggt     249
Leu Ile Glu Thr Trp Asn Pro Asn Asn Lys Pro Phe Gln Cys Ala Gly
                 55                  60                  65 gtt gcc ctc tct cgc tgc acc ctc aac cgc aac gcc ctt cgt aga cct     297
Val Ala Leu Ser Arg Cys Thr Leu Asn Arg Asn Ala Leu Arg Arg Pro
             70                  75                  80 tcc tac acc aac ggt ccc cag gaa atc tac atc caa caa ggt aag ggt     345
Ser Tyr Thr Asn Gly Pro Gln Glu Ile Tyr Ile Gln Gln Gly Lys Gly
         85                  90                  95 att ttt ggc atg ata tac ccg ggt tgt cct agc aca ttt gaa gag cct     393
Ile Phe Gly Met Ile Tyr Pro Gly Cys Pro Ser Thr Phe Glu Glu Pro
    100                 105                 110
```

```
caa caa cct caa caa aga gga caa agc agc aga cca caa gac cgt cac        441
Gln Gln Pro Gln Gln Arg Gly Gln Ser Ser Arg Pro Gln Asp Arg His
115                 120                 125                 130 cag aag atc tat aac ttc aga gag ggt gat ttg atc gca gtg cct act        489
Gln Lys Ile Tyr Asn Phe Arg Glu Gly Asp Leu Ile Ala Val Pro Thr
                135                 140                 145 ggt gtt gca tgg tgg atg tac aac aat gaa gac act cct gtt gtt gcc        537
Gly Val Ala Trp Trp Met Tyr Asn Asn Glu Asp Thr Pro Val Val Ala
        150                 155                 160 gtt tct att att gac acc aac agc ttg gag aac cag ctc gac cag atg        585
Val Ser Ile Ile Asp Thr Asn Ser Leu Glu Asn Gln Leu Asp Gln Met
            165                 170                 175 cct agg aga ttc tat ctt gct ggg aac caa gag caa gag ttt cta aaa        633
Pro Arg Arg Phe Tyr Leu Ala Gly Asn Gln Glu Gln Glu Phe Leu Lys
        180                 185                 190 tat cag caa gag caa gga ggt cat caa agc cag aaa gga aag cat cag        681
Tyr Gln Gln Glu Gln Gly Gly His Gln Ser Gln Lys Gly Lys His Gln
195                 200                 205                 210 caa gaa gaa gaa aac gaa gga ggc agc ata ttg agt ggc ttc acc ctg        729
Gln Glu Glu Glu Asn Glu Gly Gly Ser Ile Leu Ser Gly Phe Thr Leu
                215                 220                 225 gaa ttc ttg gaa cat gca ttc agc gtg gac aag cag ata gcg aaa aac        777
Glu Phe Leu Glu His Ala Phe Ser Val Asp Lys Gln Ile Ala Lys Asn
            230                 235                 240 cta caa gga gag aac gaa ggg gaa gac aag gga gcc att gtg aca gtg        825
Leu Gln Gly Glu Asn Glu Gly Glu Asp Lys Gly Ala Ile Val Thr Val
        245                 250                 255 aaa gga ggt ctg agc gtg ata aaa cca ccc acg gac gag cag caa caa        873
Lys Gly Gly Leu Ser Val Ile Lys Pro Pro Thr Asp Glu Gln Gln Gln
    260                 265                 270 aga ccc cag gaa gag gaa gaa gaa gag gat gag aag cca cag tgc            921
Arg Pro Gln Glu Glu Glu Glu Glu Glu Asp Glu Lys Pro Gln Cys
275                 280                 285                 290 aag ggt aaa gac aaa cac tgc caa cgc ccc cga gga agc caa agc aaa        969
Lys Gly Lys Asp Lys His Cys Gln Arg Pro Arg Gly Ser Gln Ser Lys
                295                 300                 305 agc aga aga aat ggc att gac gag acc ata tgc acc atg aga ctt cgc       1017
Ser Arg Arg Asn Gly Ile Asp Glu Thr Ile Cys Thr Met Arg Leu Arg
            310                 315                 320 cac aac att ggc cag act tca tca cct gac atc tac aac cct caa gcc       1065
His Asn Ile Gly Gln Thr Ser Ser Pro Asp Ile Tyr Asn Pro Gln Ala
        325                 330                 335 ggt agc gtc aca acc gcc acc agc ctt gac ttc cca gcc ctc tcg tgg       1113
Gly Ser Val Thr Thr Ala Thr Ser Leu Asp Phe Pro Ala Leu Ser Trp
    340                 345                 350 ctc aga ctc agt gct gag ttt gga tct ctc cgc aag aat gca atg ttc       1161
Leu Arg Leu Ser Ala Glu Phe Gly Ser Leu Arg Lys Asn Ala Met Phe
355                 360                 365                 370 gtg cca cac tac aac ctg aac gcg aac agc ata ata tac gca ttg aat       1209
Val Pro His Tyr Asn Leu Asn Ala Asn Ser Ile Ile Tyr Ala Leu Asn
                375                 380                 385 gga cgg gca ttg ata caa gtg gtg aat tgc aac ggt gag aga gtg ttt       1257
Gly Arg Ala Leu Ile Gln Val Val Asn Cys Asn Gly Glu Arg Val Phe
            390                 395                 400 gat gga gag ctg caa gag gga cgg gtg ctg atc gtg cca caa aac ttt       1305
Asp Gly Glu Leu Gln Glu Gly Arg Val Leu Ile Val Pro Gln Asn Phe
        405                 410                 415 gtg gtg gct gca aga tca cag agt gac aac ttc gag tat gtg tca ttc       1353
Val Val Ala Ala Arg Ser Gln Ser Asp Asn Phe Glu Tyr Val Ser Phe
```

-continued

```
            420                 425                 430
aag acc aat gat aca ccc atg atc ggc act ctt gca ggg gca aac tca    1401
Lys Thr Asn Asp Thr Pro Met Ile Gly Thr Leu Ala Gly Ala Asn Ser
435                 440                 445                 450 ttg ttg aac gca tta cca gag gaa gtg att cag cac act ttc aac cta    1449
Leu Leu Asn Ala Leu Pro Glu Glu Val Ile Gln His Thr Phe Asn Leu
                455                 460                 465 aaa agc cag cag gcc agg cag ata aag aac aac aac cct ttc aag ttc    1497
Lys Ser Gln Gln Ala Arg Gln Ile Lys Asn Asn Asn Pro Phe Lys Phe
                470                 475                 480 ctg gtt cca cct cag gag tct cag aag aga gct gtg gct tagagccctt    1546
Leu Val Pro Pro Gln Glu Ser Gln Lys Arg Ala Val Ala
                485                 490                 495 tttgtatgtg ctaccccact tttgtctttt tggcaatagt gctagcaacc aataaataat    1606
aataataata atgaataaga aaacaaaggc tttagcttgc cttttgttca ctgtaaaata    1666
ataatgtaag tactctctat aatgagtcac gaaacttttg cgggaataaa aggagaaatt    1726
ccaatgagtt ttctgtc                                                   1743
```

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer for
      amplifying Glutelin gene

<400> SEQUENCE: 2
cagcagctat taggccagag cactag                                         26

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer for
      amplifying Glutelin gene

<400> SEQUENCE: 3
gggaagcttt atccgcaagc cgacctaag                                      29

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer for
      amplifying Glutelin gene

<400> SEQUENCE: 4
cagctattta atcccagcac aaaccc                                         26

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer for
      amplifying Glutelin gene

<400> SEQUENCE: 5
gggaagctta cattactctg aggtctcgc                                      29

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:  Primer for
      amplifying Glutelin gene

<400> SEQUENCE: 6
ttcagttcca gagagcagcc                                                       20

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:  Primer for
      amplifying Glutelin gene

<400> SEQUENCE: 7
cgcggatcca tacaaaaagg gctctaag                                              28
```